United States Patent
Delaquis (10) Patent No.: US 8,242,259 B2
(45) Date of Patent: Aug. 14, 2012

(54) CELLULOSE PRODUCTION BY FACULTATIVELY ANAEROBIC MICROORGANISMS

(75) Inventor: Pascal Delaquis, Summerland (CA)

(73) Assignee: Her Majesty the Queen in right of Canada, as represented by the Minister of Agriculture and Agri-Food Canada, Saskatoon (CA)

( * ) Notice: Subject to any disclaimer, the term of this patent is extended or adjusted under 35 U.S.C. 154(b) by 190 days.

(21) Appl. No.: 12/875,011

(22) Filed: Sep. 2, 2010

(65) Prior Publication Data

US 2010/0330621 A1 Dec. 30, 2010

Related U.S. Application Data

(62) Division of application No. 11/289,703, filed on Nov. 30, 2005, now Pat. No. 7,811,795.

(51) Int. Cl.
*C08B 37/00* (2006.01)
*C12P 19/04* (2006.01)

(52) U.S. Cl. .......................... 536/56; 435/101; 435/873

(58) Field of Classification Search .................... 536/56; 435/101, 873
See application file for complete search history.

(56) References Cited

OTHER PUBLICATIONS

Cosenza and Podgwaite, "A new species of Proteus isolated from larvae of the gypsy moth *Porthetria dispar* (L.)," Antonie van Leeuwenhoek 32:187-191, 1966.*

* cited by examiner

*Primary Examiner* — Rosanne Kosson
(74) *Attorney, Agent, or Firm* — Gowling Lafleur Henderson LLP

(57) ABSTRACT

A method for producing bacterial cellulose, said method comprising culturing a biologically pure culture of a cellulose-producing *Proteus* strain in a liquid medium suitable for culturing facultatively anaerobic microorganisms, separating bacterial cellulose produced in said liquid medium from said liquid medium, washing said separated bacterial cellulose and drying said bacterial cellulose. The cellulose-producing *Proteus* strain is preferably a *Proteus myxofaciens* strain, preferably strain IDAC 071005-01 or strain ATCC 19692. The liquid medium is provided with a carbohydrate substrate containing at least one sugar selected from the group consisting of glucose, sucrose, fructose, lactose, xylose, and rhamnose. A bacterial cellulose product produced by culturing a biologically pure culture of a cellulose-producing *Proteus* strain in a liquid medium suitable for culturing facultatively anaerobic microorganisms.

10 Claims, 8 Drawing Sheets

CELLULOSE PRODUCTION BY FACULTATIVELY ANAEROBIC MICROORGANISMS

CROSS-REFERENCE TO RELATED APPLICATIONS

This application is a division of application Ser. No. 11/289,703, filed Nov. 30, 2005, now U.S. Pat. No. 7,811,795, issued on Oct. 12, 2010.

FIELD OF THE INVENTION

This invention relates to microbial production of cellulose. More particularly, this invention relates to production of microbial cellulose by facultatively anaerobic microorganisms.

BACKGROUND OF THE INVENTION

It is well-known that naturally-occurring strains of the Gram-negative microorganism *Acetobacter xylinum*, also known as *Gluconoacetobacter xylinum* (see Yamada et al., 1998, Int. J. Syst. Bacteriol. 48:327-328), are able to produce and secrete significant quantities of cellulose when grown under small-scale laboratory culture conditions wherein each microbial cell produces a single strand of cellulose commonly referred to as a strand or a fibril. Each fibril comprises multiple inter-twisted cellulose chains or microfibrils. The biochemical basis, genetics and regulation of cellulose biosynthesis in *Acetobacter xylinum* have been extensively studied, reported, and reviewed. *Acetobacter* spp. are obligate aerobic microorganisms, i.e., they have a strict requirement for $O_2$ for respiration which drives their metabolism, growth and cellulose production. When grown in standing i.e., non-shaken/agitated, liquid cultures, *Acetobacter xylinum* produces pellicles comprising disorganized layers of long intertwined cellulose strands at the interfaces between the air and liquid media. As the extent and thickness of the cellulose-containing pellicle layers increase in such standing cultures, they increasingly impede then stop $O_2$ availability from the headspace above the pellicles to the *Acetobacter* cells underlying the pellicles thus limiting and stopping cellulose production. Although cellulose produced by *Acetobacter* spp. in standing liquid cultures is chemically similar to cellulose produced from wood pulp, the major difference is that the cross-sectional diameter of *Acetobacter* spp. cellulose fibrils is usually about 2 orders of magnitude smaller than cellulose fibrils from wood. Typically, the cross-sectional dimensions of microfibrils produced by *Acetobacter* spp. is about 1.6 nm×5.8 nm, and they are twisted together to form fibrils (i.e., strands) having cross-sectional dimensions of about 3.2 nm×133 mm.

Cellulose production can be increased by culturing *Acetobacter* spp. in agitated liquid media wherein $O_2$ availability to individual *Acetobacter* spp. cells is increased through dissolved $O_2$ continually dispersed within and throughout the liquid media. Cellulose produced by *Acetobacter* spp. grown in such culture conditions is localized in multiple pellets circulating throughout the media. U.S. Pat. No. 4,863,565 and related U.S. Pat. Nos. 5,079,162, 5,144,162, 5,871,978, and 6,329,192 disclose that the macroscopic structure of cellulose in pellets produced by *Acetobacter* spp. cultured in agitated liquid media is characterized by a three-dimensional reticulated lattice structure that is significantly different from the layered cellulose macrostructure produced in pellicles from standing liquid cultures. The reticulated cellulose structure from liquid cultures is characterized by elongated strands of cellulose interconnected by shorter cellulosic branches or filaments having cross-section diameters of 0.1µ to 0.2µ, thereby forming grid-like patterns extending in three dimensions. The formation of the shorter cellulosic branches or filaments is apparently caused by one or more cellulose microfibrils separating out from the main fibril produced by an *Acetobacter* spp. cell as a result of the constant culture agitation. The shorter cellulosic branches interconnect and commingle with cellulose fibrils produced by other *Acetobacter* spp. cells thereby giving rise to the grid-like lattice structure. It also appears that the rates of agitation of liquid cultures significantly affect (a) the physical properties of the cellulose fibrils, strands, branches and filaments formed by *Acetobacter* spp., and (b) the degree of interconnecting and commingling that occurs; a low rate of agitation will result in the formation of larger cellulose-containing pellets while increasingly higher rates of agitation produce increasingly smaller cellulose pellets.

There are numerous problems encountered in attempting to scale cellulose production by *Acetobacter* spp. in large volumes of liquid media. For example, it appears that naturally occurring strains of cellulose-producing *Acetobacter* spp. are unstable when cultured in shaken or agitated liquid cultures and commonly spontaneously mutate into cellulose non-producing variants thereby limiting *Acetobacter* spp. cellulose production potential. As liquid culture volumes are increased, increasingly larger impellers and faster rates of impeller speeds are necessary to produce and maintain the levels of dissolved $O_2$ required to sustain *Acetobacter* spp. respiration, metabolism and cellulose production. U.S. Pat. No. 4,863,565 and related U.S. Pat. Nos. 5,079,162, 5,144,162, 5,871,978, and 6,329,192, and 6,329,192 teach that shear forces in liquid media caused by high impeller speeds significantly reduce the sizes of the three-dimensional reticulated cellulose structures produced by *Acetobacter* spp. thereby substantially degrading the properties of the cellulose product and its commercial usefulness. Yet another problem commonly associated with cellulose production by *Acetobacter* spp. in both standing and agitated cultures is the propensity of these microorganisms to convert glucose to gluconic acid and/or keto-gluconic acid thereby significantly dropping the pH of the media resulting in cessation of cellulose production. Furthermore, the conversion of glucose to gluconic and keto-gluconic acids decreases glucose availability for cellulose production.

Strategies developed to address cellulose production problems associated with *Acetobacter* spp. include: (1) creating mutants with reduced propensity for converting glucose into acids (e.g., U.S. Pat. No. 5,079,162) or alternatively, with modified carbohydrate and/or amino acid metabolism thereby increasing rates of cellulose production (e.g., U.S. Pat. Nos. 5,962,278, 6,110,712 and 6,140,105), (2) adding cell-division inhibitors to modify and perhaps improve the physical structure and properties of cellulose produced in agitated liquid cultures (e.g., U.S. Pat. Nos. 6,060,289 and 6,627,419), (3) increasing the availability of dissolved $O_2$ in large-volume vessels by combining two different-shaped impellers to concurrently aerate and agitate liquid media (e.g., U.S. Pat. No. 6,013,490), (4) increasing $O_2$ availability in liquid cultures contained within vessels by increasing the amount of aeration introduced into the vessel, thereby reducing the partial pressure of $CO_2$ while increasing the partial pressure of $O_2$ (e.g., U.S. Pat. No. 6,017,740), and (5) post-harvest processing methods for *Acetobacter* spp. cellulose produced in agitated liquid cultures to improve its physical properties (e.g., U.S. Pat. No. 6,153,413). However, such strategies are complicated, costly and still have the challenge of providing sufficient $O_2$ to enable optimal metabolism and cellulose production by *Acetobacter* spp. in large-volume liquid cultures.

It is well-known that other genera of obligate aerobic Gram-negative microorganisms are able to produce small amounts of cellulose from various carbon substrates under carefully controlled conditions. Such obligate aerobic cellulose-producing microorganisms include *Pseudomonas* sp., *Alcaligenes* sp., *Achromobacter* sp., *Aerobacter* sp., *Azotobacter* sp., *Agrobacterium* sp., and *Rhizobium* sp. isolated from sewage samples (Deinema et. al., 1971, Arch. Mikrobiol. 78:42-57), *Rhizobium* sp. isolated from leguminous plants (Napoli et al., 1975, Appl. Microbiol. 30:123-131), and *Agrobacterium tumefaciens* (Mathysse et al., 1995, J. Bacteriol. 177:1069-1075). However, the amounts of cellulose produced by these microbial genera are small relative to their carbon substrate inputs, and also, when compared to cellulose production by *Acetobacter* spp. Deinema et al. show in their FIGS. 1-6 on page 45 (1971, Arch. Mikrobiol. 78:42-57) that *Pseudomonas* sp., *Aerobacter* sp., *Agrobacterium* sp., and *Azotobacter* sp. produced cellulose fibrils that were branched, i.e., with microfibrils extending away from the fibrils, when grown in shaken liquid cultures. They also show in FIGS. 12 and 13 on page 48, that *Pseudomonas* strain (V-19-Ia) grown under the same shaken liquid culture conditions, produced elongated un-branched cellulose fibrils.

More recently, cellulose production and involvement in biofilm formation have been demonstrated in facultative anaerobic Gram negative bacteria including *Escherichia coli*, *Klebsiella pneumoniae* and *Salmonella enterica* (Nobles et al., 2001, Plant Physiol. 127:529-542). These species produce minute amounts of cellulose and are not expected to be of value for large-scale production.

SUMMARY OF THE INVENTION

The exemplary embodiments of the present invention, at least in preferred forms, are directed to the production of bacterial cellulose by facultatively anaerobic microorganisms.

According to one specific embodiment of the present invention, there is provided a biologically pure culture of a cellulose-producing strain of *Proteus* sp. as exemplified by *Proteus myxofaciens*. In a preferred form, there is provided a biologically pure culture of cellulose-producing *Proteus myxofaciens* strain IDAC 071005-01. However, the embodiments of the present invention include cellulose production with *Proteus myxofaciens* strain ATCC 19692.

According to another preferred embodiment of the present invention, there is provided a method for production of bacterial cellulose wherein a cellulose-producing strain of *Proteus* sp. is cultured in a liquid medium suitable for culturing facultatively anaerobic microorganisms, separating bacterial cellulose produced in said liquid medium from the liquid medium, washing said separated bacterial cellulose and drying said bacterial cellulose.

In a preferred form, the liquid medium is provided with a carbohydrate substrate containing therein at least one sugar selected from the group consisting of glucose, sucrose, fructose, lactose, xylose, and rhamnose.

In another preferred form, the liquid medium is provided with a pH selected from the range of 5 to 10, more preferably from the range of 6 to 9, and most preferably in the range of 7 to 8.5.

In yet another preferred form, the liquid medium is provided with a buffer. The buffer preferably comprises at least one of a sodium chloride buffer or a phosphate buffer, and more preferably, comprises a mixture of sodium chloride and phosphate buffers.

According to one aspect of the present invention, the method for producing bacterial cellulose comprises culturing a cellulose-producing strain of *Proteus* sp. in a liquid medium suitable for culturing facultatively anaerobic microorganisms under aerobic conditions. In a preferred form, the cellulose-producing strain is *Proteus myxofaciens* IDAC 071005-01. In another preferred form, the cellulose-producing strain is *Proteus myxofaciens* strain ATCC 19692.

According to another aspect of the present invention, the method for producing bacterial cellulose comprises culturing a cellulose-producing strain of *Proteus* sp. in a liquid medium suitable for culturing facultative anaerobic microorganisms under anaerobic conditions. In a preferred form, the cellulose-producing strain is *Proteus myxofaciens* IDAC 071005-01. In another preferred form, the cellulose-producing strain is *Proteus myxofaciens* strain ATCC 19692.

According to further preferred embodiment of the present invention, there is provided a bacterial cellulose product produced by a cellulose-producing strain of a *Proteus* sp. In a preferred form, the cellulose-producing strain is *Proteus myxofaciens* IDAC 071005-01. In another preferred form, the cellulose-producing strain is *Proteus myxofaciens* strain ATCC 19692

Deposit of the Microorganism

Samples of *Proteus myxofaciens* strain PARC-59 were deposited under the terms of the Budapest Treaty at the INTERNATIONAL DEPOSITORY AUTHORITY OF CANADA (IDAC) of 1015 Arlington Street, Winnipeg, Manitoba, R3E 3R2, Canada (Telephone: 204-789-6030; Facsimile: 204-789-2018). The deposit was made on Oct. 7, 2005 and was assigned accession number 071005-01.

BRIEF DESCRIPTION OF THE DRAWINGS

The present invention will be described in conjunction with reference to the following drawings, in which.

DETAILED DESCRIPTION OF THE INVENTION

Facultatively anaerobic microorganisms can proliferate and produce extracellular products both in the presence and the absence of oxygen. When oxygen is present in their culture media, obligate aerobes and facultative anaerobes will utilize the oxygen to oxidize carbohydrates thereby producing energy in the form of ATP along with substrates required for subsequent cellular metabolism, growth and productivity. Oxygen serves as the terminal electron acceptor in the electron transport chain by which ATP is produced. When oxygen is limiting or absent from their culture media, obligate aerobic microorganisms such as *Acetobacter* spp. are unable to oxidize carbohydrates resulting in the cessation of energy production, subsequent metabolism and growth. However, facultatively anaerobic microorganisms are able to utilize a wide variety of other compounds as alternative terminal electron acceptors for the electron transport chain in a process known as anaerobic respiration. Examples of compounds that may be utilized by facultative anaerobes for anaerobic respiration include nitrogenous compounds such as nitrates and nitrites, sulfur compounds such as sulfates, sulfites, sulfur dioxide, and elemental sulfur, carbon dioxide, iron compounds, and manganese compounds. Consequently, compared to obligate aerobic microorganisms, facultative anaerobes are easier to produce and maintain in large-volume fermentation production systems, and do not require the same complexity of culture media and equipment configurations.

According to Bergey's Manual of Systematic Bacteriology, Vol. 1 (1968), facultative anaerobic Gram-negative microorganisms generally belong to one of three families, i.e., Family I—Enterobacteriaceae, Family II—Vibrionaceae, and Family III—Pasteurellaceae. The Family Enterobacteriaceae is made up of 13 genera which are widely distributed throughout the world. They are commonly found in soil and water systems, and also are present as normal internal and external flora in humans and animals. Their host range includes insects, avians, mammals, as well as plants including fruits, vegetables, grains, flowers and trees. Many species of Enterobacteriaceae are pathogens of animals, avian sp., mammals or plants and consequently, this Family has been widely studied. In general terms, Enterobacteriaceae are Gram-negative rod-shaped bacteria that are 0.3-1.0 µm×1.0-6.0 µm. Most grow well on simple media containing a monosaccharide as a carbon source at temperatures in the range of 22° C. to 35° C. *Escherichia coli* is the type species for Enterobacteriaceae and is considered to be the most thoroughly studied of all species of bacteria because of its ease of isolation, ease of cultivation, rapid generation time, and its ability to be genetically manipulated. As a result, a wide variety of commercial fermentation processes, systems and culture media are known for the production of extracellular compounds by genetically engineered *E. coli* for use in pharmaceutical and industrial applications.

The Genus *Proteus* is classified within the Enterobacteriaceae Family and currently consists of 5 named species, i.e., *P. mirabilis, P. penneri, P. vulgaris, P. hauseri*, and *P. myxofaciens* and three unnamed genomospecies i.e., *Proteus* genomospecies 4, 5, and 6. All of the known *Proteus* sp. are ubiquitous in terrestrial environments, and some species, e.g., *P. vulgaris* and *P. mirabilis*, are common components of the normal intestinal flora in humans and animals. All *Proteus* sp. and strains are characterized by their propensity for: (a) swarming, i.e., movement of cells in periodic cycles of migration and consolidation, when cultured on solid agar media, and (b) production of extracellular slime.

*Proteus myxofaciens* is a unique but very rare specie isolated from living and dead gypsy moth larvae by Cosenza and Podgewaite who disclosed and characterized this species in 1966 in Antonie Leeuwenhoek J. Microbiol. Serol. Vol. 32 pages 187-191. They deposited their *P. myxofaciens* isolate with the American Type Culture Collection (ATCC), P.O. Box 1549, Manassas, Va. 20108, U.S.A., under ascension number 19692. Samples of this microorganism may be purchased directly from the ATCC catalogue. Since that time, the existence and properties of the *P. myxofaciens* ATCC 19692 strain disclosed and made available by Cosenza and Podgewaite have been referred to in numerous publications, but there have been no reports of further work with and/or characterization of this specie nor have there been any reports of isolations of additional strains of *P. myxofaciens*.

The inventor of the present invention has surprisingly identified a microbial strain (referred to as "PARC-59") isolated from root and leaf surfaces of field-grown carrots, as a *Proteus myxofaciens* strain based on comparisons of the morphological, biochemical and genetic profiles of the inventor's PARC-59 isolate with the profiles of *P. myxofaciens* strain ATCC 19692. Subsequently, the inventor discovered that the *P. myxofaciens* PARC-59 strain produces copious amounts of cellulose when cultured in liquid media commonly used for propagation and maintenance of microbial cultures, both under aerobic and anaerobic conditions. Accordingly, disclosed herein is a novel *Proteus myxofaciens* cellulosic strain "PARC-59". Furthermore, the inventor surprisingly discovered that *P. myxofaciens* strain ATCC 19692 also produces significant amounts of cellulose in liquid media under both aerobic and anaerobic conditions. Accordingly, disclosed herein is the use of *Proteus myxofaciens* strains for production of cellulose in liquid media under aerobic or anaerobic conditions.

Those skilled in the art will understand that the cellulosic i.e., cellulose-producing, facultative anaerobic strains of *P. myxofaciens* disclosed herein can be cultured in a wide variety of simple and complex liquid media provided with various carbon and nitrogen sources and other mineral and/or vitamin supplements useful for culturing facultative anaerobic microorganisms. Suitable carbon sources include monosaccharides such as glucose, fructose, and galactose, disaccharides such as sucrose and maltose, and complex undefined carbohydrate sources such as molasses, either solely or in selected mixtures thereof. Suitable nitrogen sources include purified amino acids, nitrates, ammonium salts, and complex undefined nitrogen-rich materials such as yeast extract, malt extract, casein and corn steep liquors, either solely or in selected mixtures thereof.

The cellulosic strains of *P. myxofaciens* of the present invention may be grown in liquid media in any vessel or reactor that can be controllably provided with a growth media contained within the vessel or reactor. Because the cellulosic strains of the present invention are facultative anaerobes, it isn't necessary to provide high-speed agitation to generate turbulent flows of liquid media in order to maintain target levels of dissolved $O_2$. Accordingly, those skilled in the fermentation arts will understand how to combine and configure various types of fermenter vessels and reactors with a variety of equipment including impellers and/or fluid circulation pumps to provide single-batch, repeated-batch, or continuous fermentation systems with suitable replenishment of liquid media therein for cellulose production by the cellulosic facultative anaerobic microorganisms disclosed herein. The cellulose produced in such liquid cultures may be harvested by the same equipment and methods used in the art to harvest particulate or precipitated extracellular products or alternatively, cellular debris from other types of large-volume microbial fermentations. An example of a preferred harvesting system is continuous centrifugation of the liquid culture through a stacked-disk multichamber centrifuge wherein a large effective surface area is provided for collecting thereon attached microorganisms including extracellular products such as the cellulose produced by the facultative anaerobic of the present invention. The harvested cellulose should then be washed with water and pressed or centrifuged to remove residual media after which the washed cellulose product of the present invention can be purified by heating to at least 100° C. in an alkaline solution of 1N sodium hydroxide for an appropriate period of time based on the volume of cellulose product being purified. The alkaline solution may be removed by pressing or continual centrifugation and the purified cellulose washed in water, then collected and dried into its final product form.

Since both the ATCC 19692 strain of *P. myxofaciens* and the IDAC 071005-01 strain, which were obtained from quite different sources, produce cellulose, it appears that this is a basic biological process of *P. myxofaciens* that will be exhibited by all strains of the microorganism.

The cellulosic facultative anaerobic microorganisms, methods employing said cellulosic facultative anaerobic microorganisms to produce cellulose, and the cellulose product of the present invention are described in more detail in the following examples which are intended to be exemplary of the invention and are not intended to be limiting.

Example 1

Isolation, Identification, and Characterization of a Cellulose-Producing Strain of *Proteus myxofaciens*

Field carrots grown at the Pacific Agri-Food Research Centre in Summerland, British Columbia, Canada, were harvested from the soil and sampled for assessments of the presence and prevalence of *Listeria* spp. The APHA method disclosed by Vanderzant et al. (1992, Compendium of Methods for the Microbiological Examination of Foods. $3^{rd}$ Edition. American Public Health Association, Washington, D.C. pp. 637-663) was adapted for isolation of microorganisms present on the carrots' roots and leaves as follows. Individual root and leaf sections were subjected to primary enrichment by incubation in test tubes containing in UVM *Listeria* Selective broth, followed by secondary enrichment by transferring to test tubes containing Fraser broth. Subsamples from each test tube containing Fraser broth were streaked onto Petri plates containing Oxford Agar, then incubated at 25° C. for 2 days, after which the plates were observed for the presence of typical *Listeria* colonies. Presumptive *Listeria* isolates were purified by repeated streaking onto fresh Petri plates containing Trypticase Soy agar supplemented with 5 g/L yeast extract (TSA-YE). Each purified isolate was given an ID-code number, and then inoculated into test tubes containing Trypticase Soy broth supplemented with 5 g/L yeast extract (TSB-YE), and incubated at 25° C. for 24 h in preparation for further characterizations. One microbial isolate obtained from a sample of carrot leaves and given the ID-code "PARC-59", produced a solid plug with the consistency of a gel within 24 h after inoculation. The plug physically displaced the liquid culture medium in the test tube after the 24 h incubation period. Another PARC-59 culture was streaked onto Petri plates containing TSA-YE agar, from which, it was inoculated into a test tube containing TSB-YE with similar results, i.e., a solid gel plug was produced within a 24-h incubation at room temperature, and displaced the liquid medium in the test tube.

Gram staining, oxidase and catalase tests were performed with reagents from Difco (Detroit) on 24-h PARC-59 cultures grown at 25° C. on TSB-YE agar plates. The Gram reaction was verified by the KOH method. The isolate was identified as *Proteus myxofaciens* with the BIOLOG automated microbial identification system (Hayward, Calif.) using GN (Gram-negative) microwell plates and procedures described by the manufacturer. *Proteus myxofaciens* ATCC 19692, the type strain for this species, was also inoculated in BIOLOG microplates and the carbon substrates utilized or oxidized by the two strains are shown in Table 1. Similarity indices obtained in the BIOLOG identification system were 0.859 and 0.755 for the ATCC 19692 strain and the Summerland PARC-59 isolate, respectively. Positive identification is considered acceptable when the similarity index exceeds 0.5. Accordingly, PARC-59 was confirmed as a *P. myxofaciens* strain. *Proteus myxofaciens* strain PARC-59 is referred to herein after as *Proteus myxofaciens* strain IDAC 071005-01

TABLE 1

Comparisons of the substrates utlizized or oxidized by *Proteus myxofaciens* ATCC 19692 and PARC-59 in BIOLOG

| Substrate | Biolog database | ATCC 19692 | PARC-59 |
|---|---|---|---|
| acetic acid | − | + | + |
| N-acetyl-D-glucosamine | + | + | + |
| cis-aconitic acid | + | + | + |
| alanimicide | + | + | + |
| L-alanine | − | + | + |
| L-analyl-glycine | + | + | + |
| L-arabinose | − | + | − |
| asparagine | + | + | + |
| aspartic acid | + | + | + |
| bromo-succinic acid | + | + | + |
| 2,3-butainediol | − | + | − |
| citric acid | + | + | + |
| dextrin | + | + | + |
| formic acid | + | + | + |
| D-fructose | + | + | + |
| D-galacturonic acid | − | − | + |
| galactose | + | + | + |
| gentobiose | + | + | − |
| α-D-glucose | + | + | + |
| gluconic acid | + | + | + |
| L-glutamic acid | + | + | + |
| D-glucosaminic acid | − | − | + |
| glycerol | + | + | + |
| glycogen | + | + | + |
| D,L-α-glycerol phosphate | + | + | + |
| glycyl-L-aspartic acid | + | + | + |
| glycyl-L-glutamic acid | + | + | + |
| α-hydroxybutyric acid | − | + | − |
| myoinositol | + | + | + |
| α-keto butyric acid | − | + | − |
| α-keto glutaric acid | − | + | − |
| inosine | + | + | + |
| D,L-lactic acid | + | + | + |
| α-D-lactose | − | + | + |
| lactulose | − | + | + |
| L-leucine | − | + | − |
| maltose | + | + | + |
| mannose | + | + | + |
| glycogenmethyl pyruvate | + | + | + |
| mono-methyl succinate | + | + | + |
| proline | + | + | + |
| d-psicose | + | + | + |
| D-serine | + | + | + |
| L-serine | + | + | + |
| D-sorbitol | − | + | + |
| succinamic acid | + | + | + |
| succinic acid | + | + | + |
| sucrose | + | + | + |
| L-threonine | − | + | − |
| thymidine | + | + | + |
| Trehalose | + | + | + |
| Turanose | + | + | + |
| Tween 40 | + | + | + |
| Tween 80 | + | + | + |

Example 2

Characterization of Gel Production by *P. myxofaciens* Strains IDAC 071005-01 and ATCC 19692

Individual test tubes containing 10-mL of Trypticase Soy Broth (TSB), TAB amended with yeast extract (Ig/L) (TSB-YE), APT broth (APTB), Tryptose broth (TB) and Nutrient broth (NB) were inoculated with a loopful *P. myxofaciens* ATCC 19692 or IDAC 071005-01. One tube of each strain was incubated at 6° C., 20° C., 25° C., 30° C., 35° C. and 40° C. for 48 h and then examined for evidence of microbial growth and gel formation. As shown in Table 2, the relative amounts of gel produced by the two *P. myxofaciens* strains during the incubation period varied with medium composition and temperature of incubation. Gel production was unhindered by vessel geometry and was achieved throughout deep test tubes, suggesting that synthesis of the substance was not subject to oxygen limitation. Gel formation was most extensive at 20° C. and 25° C. by both strains, but each strain produced smaller plugs comprising less solid, more viscous, buoyant material at higher incubation temperatures i.e., temperatures above 25° C. Growth by both strains was observed at 6° C. and at 40° C., but without secretion of gel. More gel was produced in APT broth and TSB-YE than any of the other media. Nutrient broth did not support gel production by either strain (Table 2) suggesting that availability of a carbohydrate substrate was essential for gel production, since NB was the only growth medium that did not contain glucose.

TABLE 2

Gel production by *P. myxofaciens* strains ATCC 19692 and IDAC 071005-01 in various media at different temperatures*

| | *P. myxofaciens* IDAC 071005-01 Growth temperature | | | | *P. myxofaciens* IDAC 071005-01 Growth temperature | | | |
|---|---|---|---|---|---|---|---|---|
| Medium | 20° C. | 25° C. | 30° C. | 35° C. | 20° C. | 25° C. | 30° C. | 35° C. |
| TSB-YE | +++ | +++ | ++ | + | +++ | +++ | ++ | + |
| TSB | ++ | ++ | ++ | + | ++ | ++ | + | + |
| APTB | +++ | +++ | ++ | − | +++ | +++ | ++ | − |
| TB | ++ | ++ | ++ | + | ++ | ++ | + | + |
| NB | − | − | − | − | − | − | − | − |

*+++ = completely gelled ++ = thick gel plug but not completely gelled + = small gel plug − = no visible gel The TSB-YE medium was further investigated because both strains produced gels in this medium at temperatures up to 25° C. Since the gels produced by both strains resisted boiling in 1N NaOH, a method based on this property was developed for purification and quantification as shown below:

Inoculate TSB-YE and incubate for 24 h (25° C.)

↓

Squeeze gel to remove excess growth medium

↓

-continued

Add 100 mL 1 N naOH

↓

Autoclave at 121° C. for 15 min or boil for 2 h

↓

Cool to room temperature and drain NaOH

↓

Add 100 mL de-ionized distilled water

↓

Put on a rotary shaker overnight

↓

Drain and replace water

↓

Put on a rotary shaker for 4 h

↓

-continued

Drain water and repeat water wash 3 times

↓

Freeze dry, weigh

Clear, translucent, turgid gels swollen with water were obtained by this procedure. Upon freeze-drying the gel collapsed into a thin, white film that could be torn similar to paper. Furthermore, the dried film did not swell when immersed in water for several days at room temperature.

The effect of sugar type and quantity on the amount of purified, freeze dried gel obtained by cultivation of both strains in supplemented TSB-YE is shown in Table 3.

TABLE 3

Amounts of purified gel produced by *P. myxofaciens* strains
ATCC 19692 and IDAC 071005-01 after 24-h growth at
25° C. in 100 Ml TSB-YE supplemented with
0.1 and 1.0 g of glucose, fructose and sucrose.
Each measurement is the mean of four replicates

| | Freeze-dried gel produced (mg) | |
|---|---|---|
| Substrate | ATCC 19692 | IDAC 071005-01 |
| 0.1 g fructose | 0 | 3.0 ± 2.0 |
| 1.0 g fructose | 5.3 ± 0.9 | 13.1 ± 0.3 |
| 0.1 g glucose | 0.3 ± 0.1 | 2.0 ± 1.0 |
| 1.0 g glucose | 6.1 ± 0.5 | 19.3 ± 0.6 |
| 0.1 g sucrose | 1.3 ± 0.2 | 7.1 ± 0.4 |
| 1.0 g sucrose | 16.0 ± 1.0 | 29.2 ± 0.5 |

Gel yields increased with sugar concentrations and were highest in TSB-YE supplemented with sucrose, followed by glucose and fructose. *P. myxofaciens* IDAC 071005-01 produced much greater amounts of gel in each treatment than did ATCC 19692, regardless of sugar substrate.

Example 3

Conversion of Sugars to Cellulose by *Proteus myxofaciens*

Figure 1:
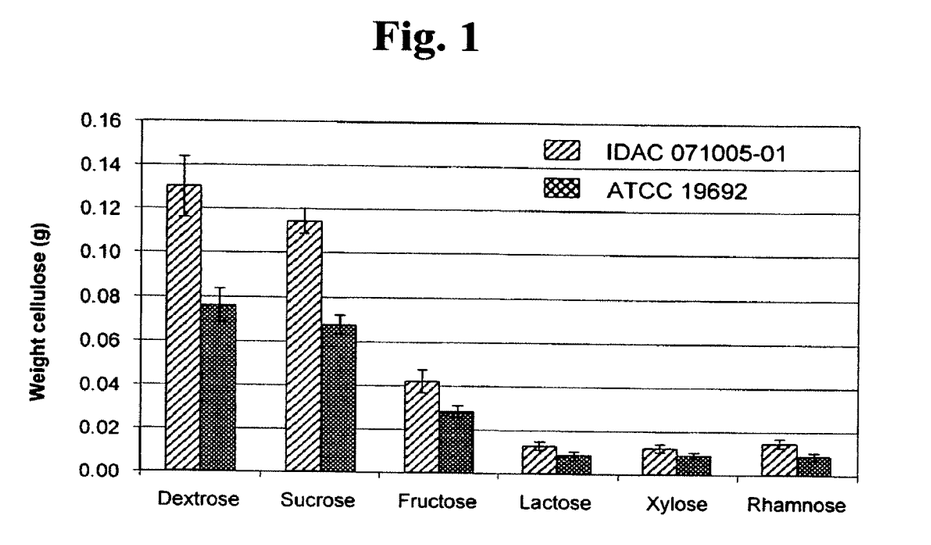
FIG. 1 is a graph showing the yields of purified bacterial cellulose obtained from various sugars with *Proteus myxofaciens* strains IDAC 071005-01 and ATCC 19692.

The ability of *P. myxofaciens* to convert different types of sugars into cellulose was assessed by the following method. The following sugars were assessed in this study: glucose, sucrose, fructose, lactose, xylose, and rhamnose. The conversion of each sugar was tested in TSB-YE liquid medium at a concentration of 10 g/L. *P. myxofaciens* strains IDAC 071005-01 and ATCC 19692 maintained on TSA-YE agar, were inoculated into Erlenmeyer flasks containing 100-ml volumes of TSB-YE amended with the individual sugars (3 replicates/sugar/strain). The inoculated Erlenmeyer flasks were then incubated at 25° C. for 48 h without agitation. Excess medium was removed from the resulting mass of cells and cellulose by application of mechanical pressure. The mass was boiled in 1 N NaOH for 2 h, and then washed three times with distilled water. The purified and washed cellulose samples were freeze-dried prior to dry weight determinations. Both *P. myxofaciens* strains converted each sugar tested into cellulose (FIG. 1). However, *P. myxofaciens* cultured in liquid media containing either glucose or sucrose produced the greatest amounts of cellulose (FIG. 1).

Figure 2:
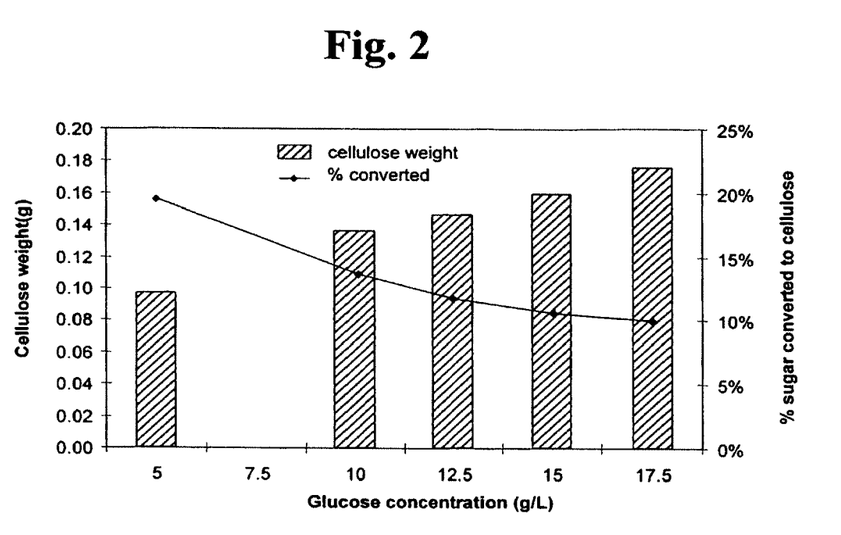
FIG. 2 is a graph showing the effects of increasing glucose levels on cellulose production by *Proteus myxofaciens* strain IDAC 071005-01.

The effects of increasing sugar concentrations in liquid media on cellulose production were assessed by inoculating *P. myxofaciens* IDAC 071005-01 into Erlenmeyer flasks containing 100-mL volumes of TSB-YE amended with one of the following concentrations of glucose: 5.0 g/L, 10.0 g/L, 12.5 g/L, 15.0 g/L and 17.5 g/L. The inoculated Erlenmeyer flasks were incubated at 25° C. for 48 h. Cellulose was then harvested from each flask after boiling in 1 N NaOH as described above. The purified and washed cellulose samples were freeze-dried prior to dry weight determinations. The data in FIG. 2 show that cellulose production was increased by increasing the concentration of sugar substrate provided in the liquid medium.

Example 4

Effects of pH on Cellulose Production by *Proteus myxofaciens*

Figure 3:
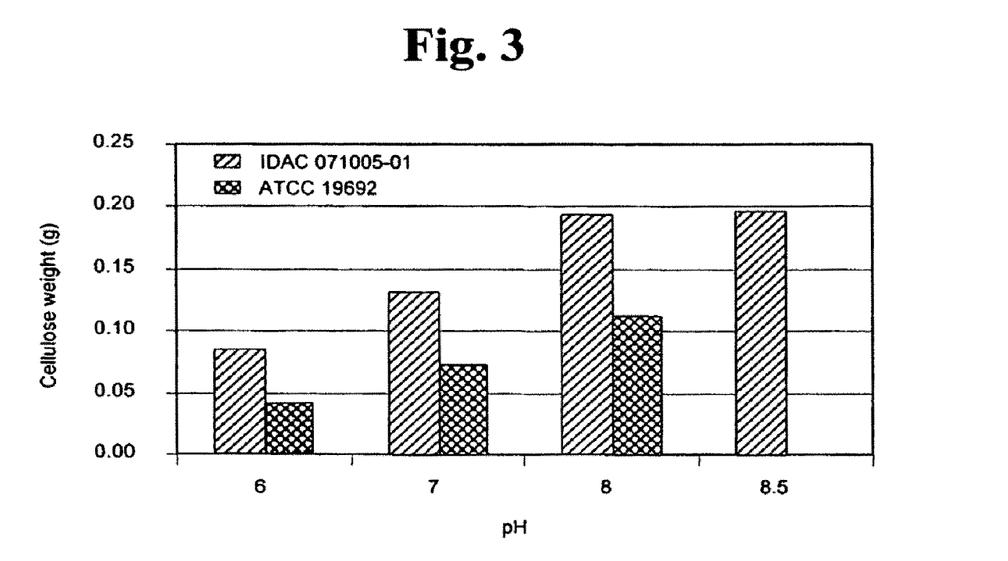
FIG. 3 is a graph showing the effects of medium pH on the production of bacterial cellulose by *Proteus myxofaciens* strains IDAC 071005-01 and ATCC 19692.

The effects of pH on cellulose production by *P. myxofaciens* were examined by culturing strains IDAC 071005-01 and ATCC 19692 in 100-mL volumes TSB-YE liquid medium amended with 10 g/L glucose adjusted to pH values of 6.0, 7.0, 8.0, and 8.5 under conditions described above. The data in FIG. 3 show that both *P. myxofaciens* strains produced more cellulose as pH levels were increased from 6 to 8.

Example 5

Effects of Media Supplements on Cellulose Production by *Proteus myxofaciens*

Figure 4:
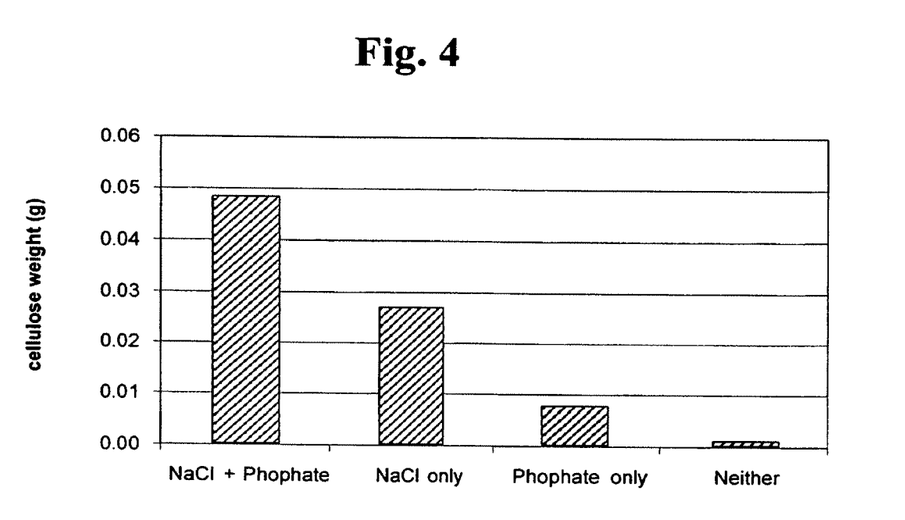
FIG. 4 is a graph showing the effects of a buffer on the production of bacterial cellulose by *Proteus myxofaciens* strain IDAC 071005-01.

The effects of various liquid media supplements including vitamins, minerals, enzyme co-factors, and buffers such as NaCl and phosphate, were individually assessed in 100-mL volumes of TSB-YE liquid medium amended with 10 g/L glucose, under conditions as described above. Addition of omission of various vitamins, minerals, and enzyme co-factors did not have any effects on the cellulose production by *P. myxofaciens* strains IDAC 071005-01 or ATCC 19692. However, the data in FIG. 4 show that optimal cellulose production was achieved when both NaCl and phosphate buffers were incorporated into the liquid culture medium, and that deletion of either buffer from the medium significantly reduced cellulose production.

Example 6

Characterization and Comparisons of Cellulose Produced by *Proteus myxofaciens* and *Acetobacter xylinum*

Figure 5:
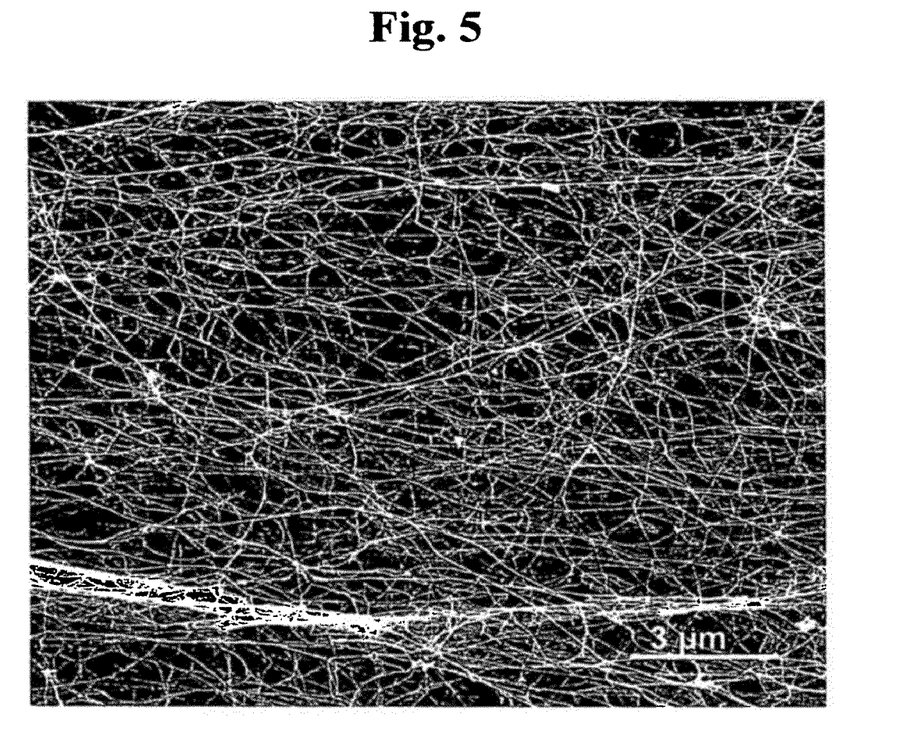
FIG. 5 is a scanning electron micrograph of the bacterial cellulose matrix produced by *Proteus myxofaciens* strain IDAC 071005-01 of the present invention.

*Proteus myxofaciens* strain IDAC 071005-01 was cultured in 100-mL of TSB-YE liquid medium amended with 10 g/L glucose adjusted to pH 8.5 under conditions described above. Samples of gel produced in the medium were removed with a razor blade, then washed and sputter coated with gold and examined in a JEOL model 840 A scanning electron microscope (Japan) at an accelerating voltage of 35 kV. The micrographs revealed a matrix of highly reticulated fibres with embedded bacterial cells (FIG. 5).

Figure 6:
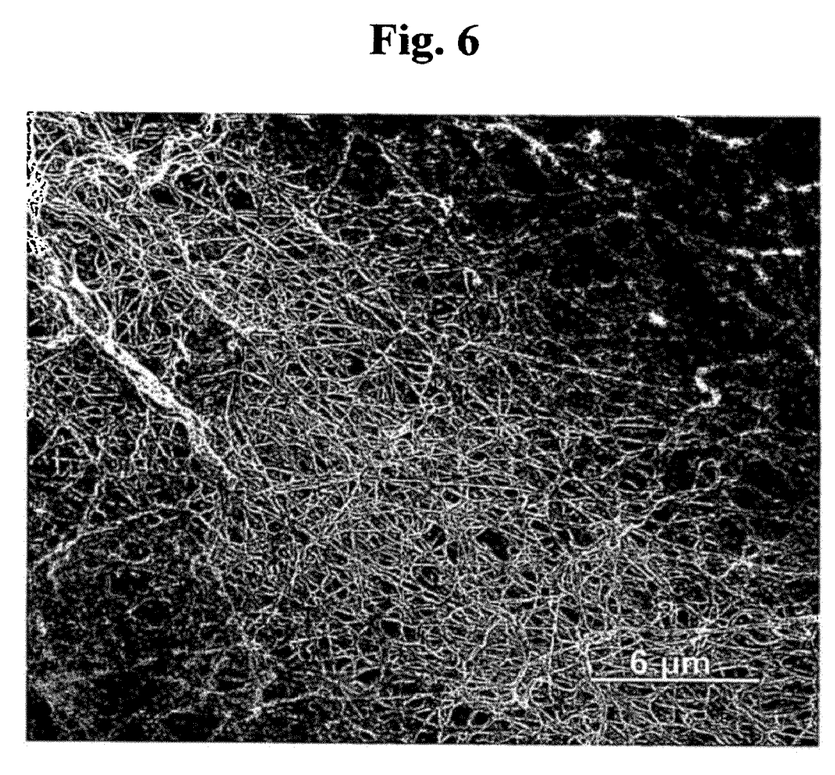
FIG. 6 is a scanning electron micrograph of the bacterial cellulose matrix produced by *Acetobacter xylinum* strain PARC 017.

*Acetobacter xylinum* strain PARC 017 (isolated from apple cider vinegar) was cultured in static culture for 14 days at 25° C. using the medium and method described by Hestrin and Schramm in Biochemistry Journal Vol. 58 on pages 345-352 (1954). A sample of the pellicle produced on the surface of the culture was removed and prepared for microscopic examination as described above. A micrograph of the bacterial cellulose produced by *Acetobacter xylinum* strain PARC 017 is shown in FIG. 6. Comparison of FIGS. 5 and 6 suggests that the physical structure and architecture of the bacterial cellulose produced by *Acetobacter xylinum* strain PARC 017 is similar to that produced by *Proteus myxofaciens* IDAC 071005-01.

Figure 7:
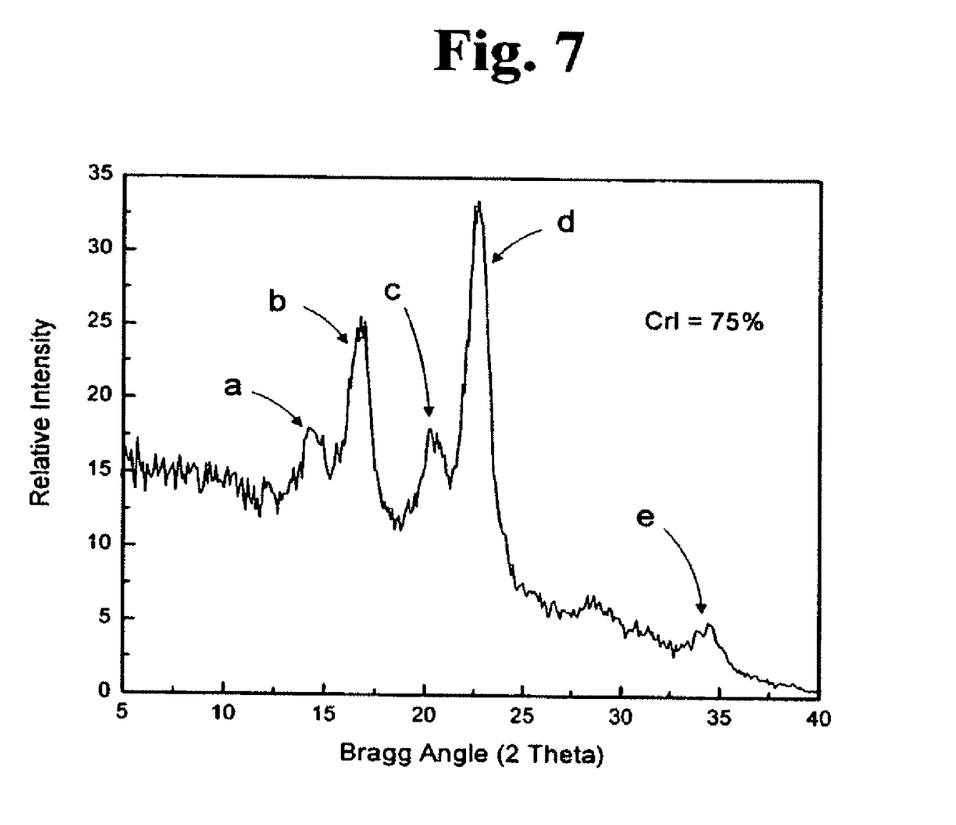
FIG. 7 is a one-dimensional micro-diffraction diagram showing the degree of crystallinity of cellulose produced by *Proteus myxofaciens* strain IDAC 071005-01.
Figure 8:
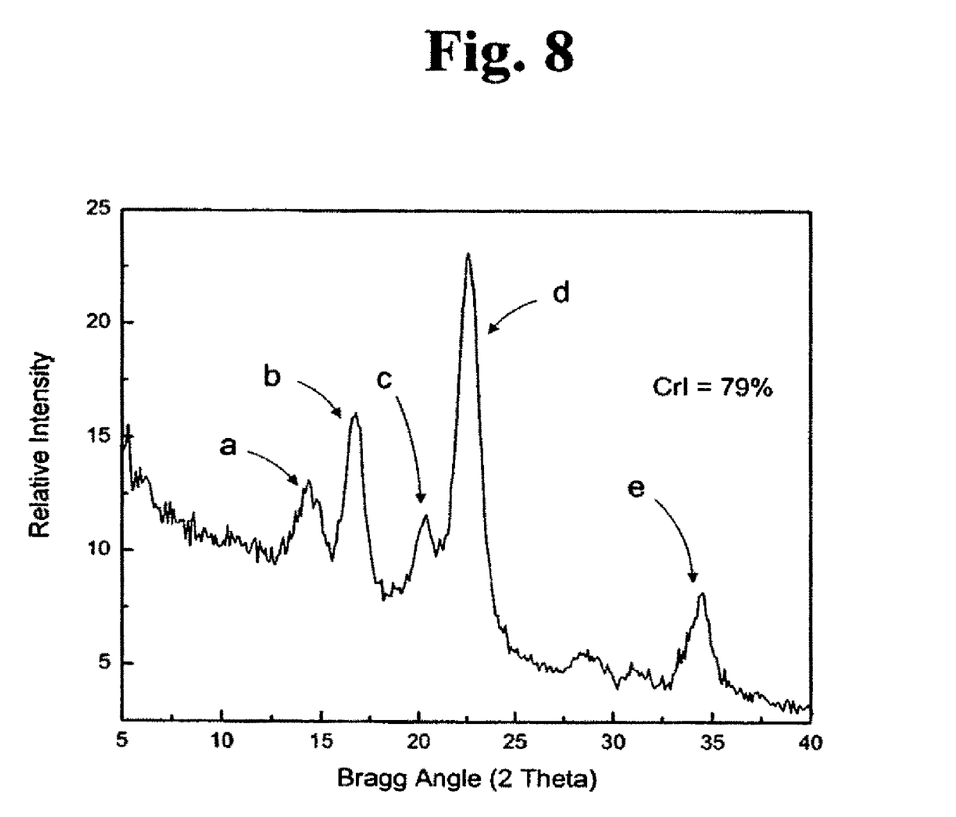
FIG. 8 is a one-dimensional micro-diffraction diagram showing the degree of crystallinity of cellulose produced by *Acetobacter xylinum* strain PARC 017.

The crystalline structures of the bacterial celluloses produced by *Proteus myxofaciens* stain IDAC 071005-01 and *Acetobacter xylinum* strain PARC 017 were measured on a Bruker D8 Discover X-Ray diffraction unit equipped with a GADDS detector. The intensities of the samples were collected over the range from $2\theta=5$ to 40. The wide-angle diffractometer was used in transmission mode, and the measurements were performed with $CuK\alpha_1$ radiation ($\lambda=1.54°$ fit with a 0.5 mm collimator and the scattered photon collected by a GADDS detector. The source was set to 0° while the detector was set to 17°. The raw data were collected and fit mathematically using the method of Vonk described in Journal of Applied Crystallography Vol. 6 on pages 148-152 (1973). The degree of crystallinity of the bacterial cellulose samples was expressed in terms of the crystallinity index (CrI) as defined by Segal et al. in Textile Research Journal Vol. 29 on pages 786-794 (1959). The X-ray defraction pattern of the bacterial cellulose produced by *Acetobacter xylinum* strain PARC 017 is shown in FIG. 7 while the X-ray defraction pattern of the bacterial cellulose produced by *Proteus myxofaciens* IDAC 071005-01 is shown in FIG. 8. Comparisons of these data indicate that while the crystalline structure of bacterial cellulose produced by *Proteus myxofaciens* is similar to that produced by *Acetobacter xylinum* strain PARC 017 as evidenced by common peaks a, b, c, d, and e which were defracted at identical Bragg Angles, it is to be noted that there may be dissimilarities between their surface architectures and topographies because the CrI of the cellulose produced by *Acetobacter xylinum* PARC 017 was 75% (FIG. 7) while the CrI of the cellulose produced by *Proteus myxofaciens* was 79% (FIG. 8).

What is claimed is:

1. A bacterial cellulose product produced by the steps of:
   culturing a biologically pure culture of a cellulose-producing *Proteus myxofaciens* strain IDAC 071005-01 in a liquid medium suitable for culturing facultatively anaerobic microorganisms;
   recovering bacterial cellulose produced in the liquid medium from the liquid medium;
   washing the recovered bacterial cellulose; and
   drying bacterial cellulose.

2. The bacterial cellulose product according to claim 1 wherein the liquid medium is suitable for culturing facultatively anaerobic microorganisms under aerobic conditions.

3. The bacterial cellulose product according to claim 1 wherein the liquid medium is suitable for culturing facultatively anaerobic microorganisms under anaerobic conditions.

4. The bacterial cellulose product according to claim 2 wherein the liquid medium is provided with a carbohydrate substrate containing therein at least one sugar selected from the group consisting of glucose, sucrose, fructose, lactose, xylose, and rhamnose.

5. The bacterial cellulose product according to claim 2 wherein the liquid medium is provided with a pH selected from the range of 5 to 10.

6. The bacterial cellulose product according to claim 2 wherein the liquid medium is provided with a pH selected from the range of 6 to 9.

7. The bacterial cellulose product according to claim 2 wherein the liquid medium is provided with a pH selected from the range of 7 to 8.5.

8. The bacterial cellulose product of claim 2, wherein the liquid medium is provided with a buffer and/or a salt.

9. The bacterial cellulose product of claim 2, wherein the buffer is a phosphate buffer.

10. The bacterial cellulose product of claim 2, wherein the salt is sodium chloride.

* * * * *